US00PP26703P3

(12) United States Plant Patent
Ilsink

(10) Patent No.: US PP26,703 P3
(45) Date of Patent: May 10, 2016

(54) *ROSA* PLANT NAMED 'INTROS02'

(50) Latin Name: ***Rosa* hybrid**
Varietal Denomination: IntRos02

(71) Applicant: Robert Ilsink, Leersum (NL)

(72) Inventor: Robert Ilsink, Leersum (NL)

(73) Assignee: Interplant Roses B.V. (NL)

( * ) Notice: Subject to any disclaimer, the term of this patent is extended or adjusted under 35 U.S.C. 154(b) by 112 days.

(21) Appl. No.: 14/120,793

(22) Filed: Jun. 27, 2014

(65) Prior Publication Data

US 2015/0382526 P1 Dec. 31, 2015

(51) Int. Cl.
*A01H 5/02* (2006.01)

(52) U.S. Cl.
USPC ..... Plt./106

(58) Field of Classification Search
USPC ..... Plt./106
See application file for complete search history.

*Primary Examiner* — Anne Grunberg
(74) *Attorney, Agent, or Firm* — Cassandra Bright

(57) ABSTRACT

A new and distinct *Rosa* cultivar named 'IntRos02' is disclosed, characterized by abundant flowering, compact form and unique flower coloration of peach petals with a red-purple blotch. The new variety is a *Rosa*, normally produced as an outdoor garden or container plant.

3 Drawing Sheets

Latin name of the genus and species: *Rosa* hybrid.
Variety denomination: 'IntRos02'.

BACKGROUND OF THE INVENTION

The new *Rosa* cultivar is a product of a planned breeding program conducted by the inventor, Robert Ilsink, in Leersum, Netherlands. The objective of the breeding program was to produce new *Rosa* varieties for ornamental commercial applications. The cross resulting in this new variety was made during April of 2004.

The seed parent is the unpatented, proprietary variety referred to as *Rosa* 'B274-02'.The pollen parent is the unpatented, proprietary variety referred to as *Rosa* 'B390-01'. The new variety was discovered in April of 2005 by the inventor in a group of seedlings resulting from the 2004 crossing, in a research greenhouse in Leersum, Netherlands.

Asexual reproduction of the new cultivar was performed by vegetative cuttings. This was first performed at a research greenhouse in Leersum, Netherlands in July of 2006 and has shown that the unique features of this cultivar are stable and reproduced true to type in more than 8 successive generations.

SUMMARY OF THE INVENTION

The cultivar 'IntRos02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IntRos02' These characteristics in combination distinguish 'IntRos02' as a new and distinct *Rosa* cultivar:

1. Red spot in center of flower, withouter petal coloration of peach.

2. Compact size.
3. Abundant flowering.

Plants of the new cultivar 'IntRos02' are similar to plants of the seed parent, *Rosa* 'B274-02' in most horticultural characteristics, however, plants of the new cultivar 'IntRos02' differs in the following:

1. Peach colored flower fading to very light purple. The seed parent has a soft yellow colored flower that fades to white.

Plants of the new cultivar 'IntRos02' are similar to plants of the pollen parent; *Rosa* 'B390-01' in most horticultural characteristics, however, plants of the new cultivar 'IntRos02' differ in the following;

1. Peach colored flower fading to very faint purple. The pollen parent has a peach colored flower that fades to soft pink.

COMMERCIAL COMPARISON

Plants of the new cultivar 'IntRos02' can also be compared to the commercial variety *Rosa* 'Interbylonbab', unpatented. These varieties are similar in most horticultural characteristics; however 'IntRos02' differs in the following:

1. Flower color fades to a very light purple. The comparator flower color fades to light yellow.
2. Less compact, more upright form. The comparator is more compact and more spreading in form.
3. Flower has an average of 8 petals. The comparator has an average of 5 petals.

BRIEF DESCRIPTION OF THE PHOTOGRAPHS

The accompanying photograph in FIG. 1 illustrates in full color a typical plant of 'IntRos02' grown in an approximately 2 gallon nursery pot. Age of the plant photographed is approximately 2 years.

Figure 1:
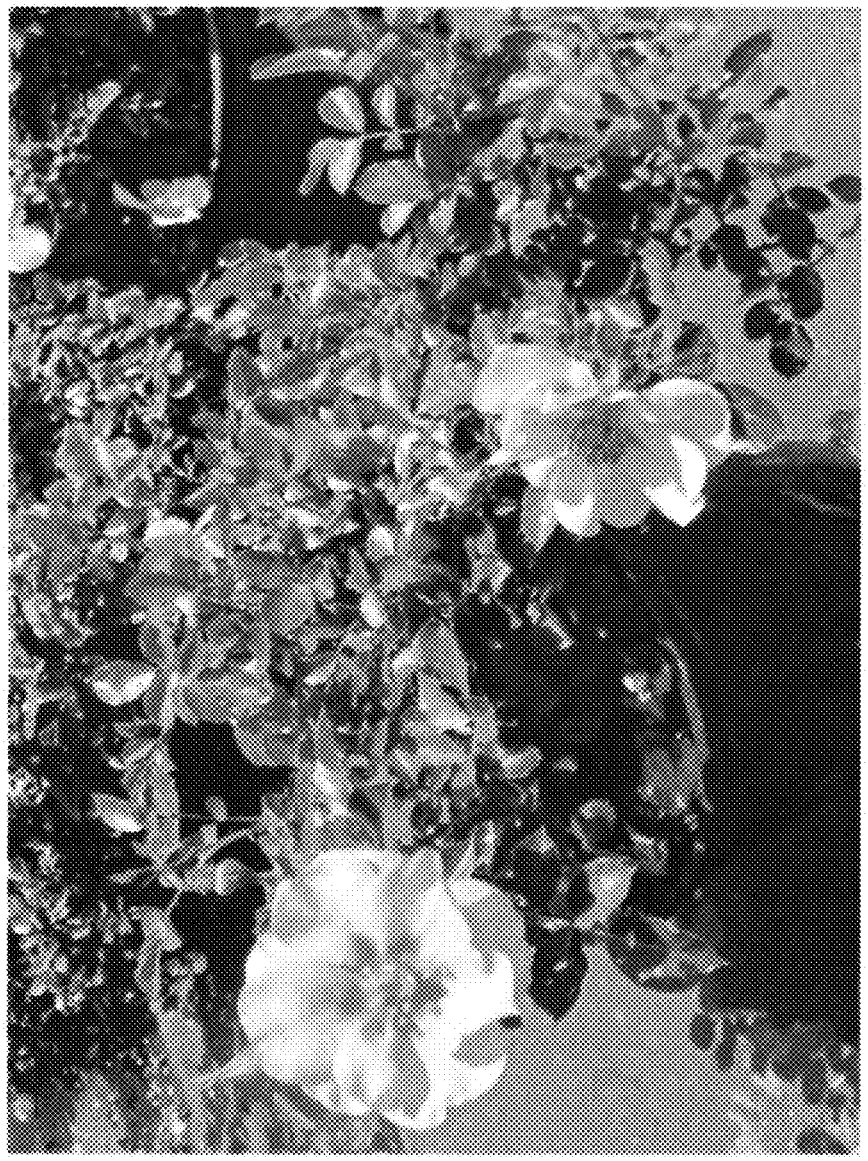
Figure 2:
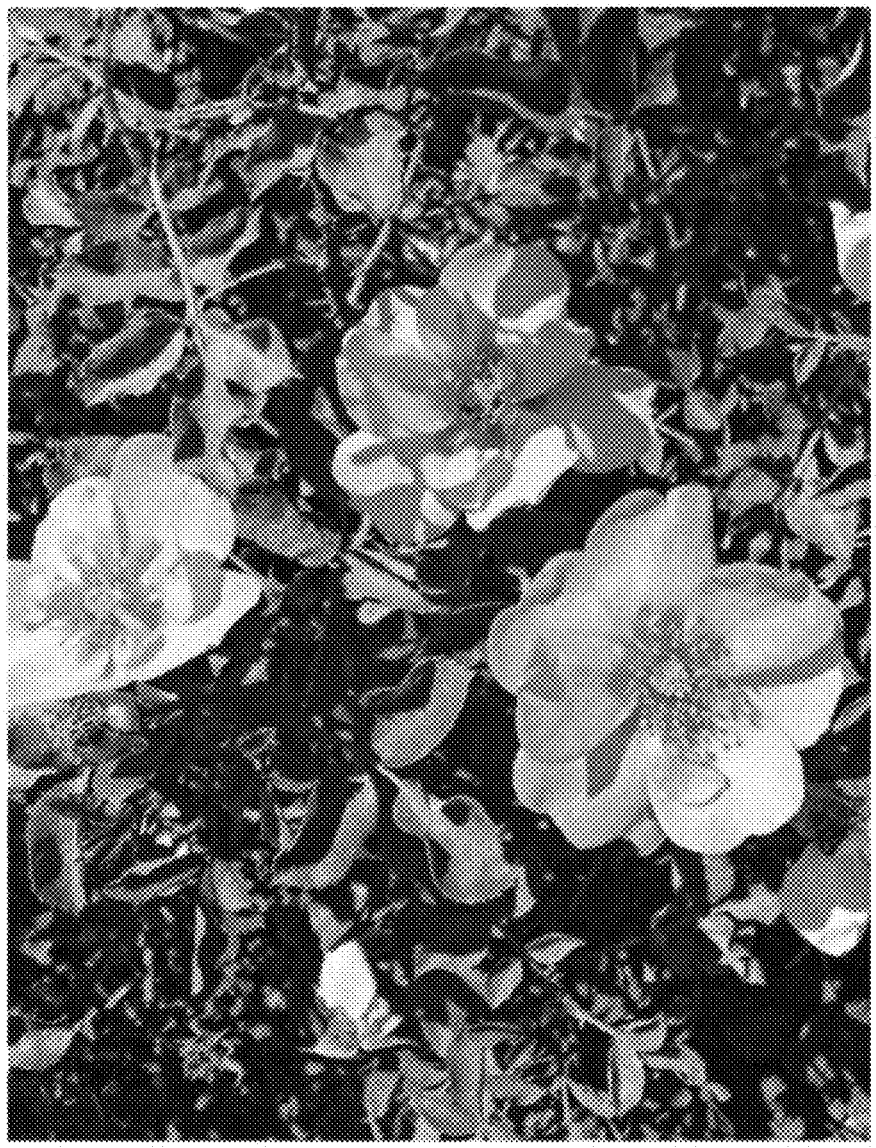
FIG. 2 illustrates a close up of multiple flowers, in various stages of maturity.
Figure 3:
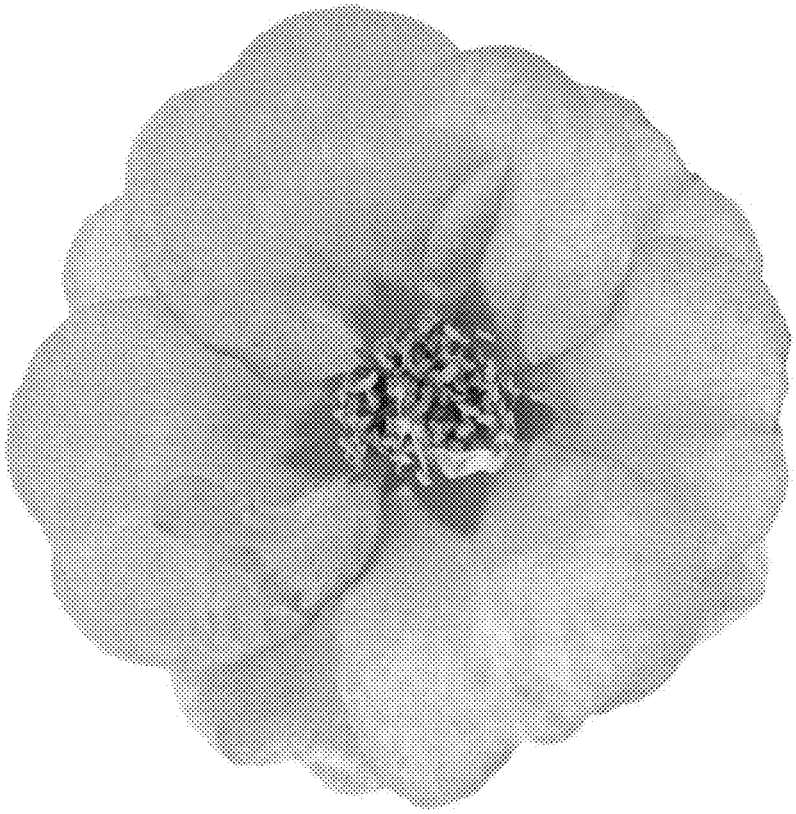
FIG. 3 illustrates a close up of a single mature flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'IntRos02' plants grown outdoors in, Leersum, Netherlands. The growing temperature ranged from approximately 0° C. to 28° C. during the day and from approximately −5° C. to 18° C. during the night. General light conditions are bright, normal sunlight. Measurements and numerical values represent averages of typical plant types.

Botanical classification: *Rosa* 'IntRos02'.

PROPAGATION

Time to initiate roots: About 15 days at approximately 20° C.

Time to produce a rooted cutting: About 35 days at approximately 20° C.

PLANT

Age of plant described: Approximately 2 years.
Growth habit: Compact spreading.
In a container or in the ground: In container.
Height: 500 mm (50 cm).
Plant spread: 500 mm (50 cm).
Rootstock: Own root.
Growth rate: Approximately 2 years to reach 0.5 meters.
Branching characteristics: Sympodial branching.
Length of primary lateral branches: Approximately 50 cm.
Diameter of lateral branches: Approximately 1 cm.
Quantity of lateral branches: Numerous.
Branching arrangement: Branching from every axillary bud possible.
Branches—young wood:
- *Diameter*.—Approximately 0.5 cm.
- *Texture*.—Herbaceous; glossy with anthocyanin coloration.
- *Approximately density of thorns*.—Dense.
- *Color*.—Near Red-Purple RHS 70A.

Branches—old wood:
- *Diameter*.—Approximately 1 cm, after 2 years.
- *Color*.—Near Green RHS 141B.
- *Texture*.—Woody; semi glossy.
- *Approximately density/quantity of thorns*.—Numerous.
- *Color of thorns*.—Red purple, closest to 59A.

FOLIAGE

Leaf:
- *Arrangement*.—Alternate.
- *Quantity*.—Approximately 6 per main branch.
- *Average length*.—Approximately 12 cm.
- *Average width*.—Approximately 8 cm.

Leaflet:
- *Quantity*.—Approximately 5 per leaf.
- *Average length*.—Approximately 4 cm.
- *Average width*.—Approximately 2.5 cm.
- *Shape of blade*.—Oval.
- *Apex*.—Pointed.
- *Base*.—Rounded.
- *Margin*.—Serrated.
- *Appearance of top surface*.—Semi glossy.
- *Appearance of bottom surface*.—Matte.
- *Texture of top surface*.—Non-pubescent.
- *Texture of bottom surface*.—Non-pubescent.
- *Leaf internode length*.—4 cm.
- *Color*.—Young foliage upper side: Near Green RHS 133B. Young foliage under side: Near RHS 133B. Mature foliage upper side: Near Green RHS 126A. Mature foliage under side: Near RHS 126A.
- *Venation*.—Type: Reticulate. Venation color upper side: Indistinguishable from leaf blade. Venation color under side: Indistinguishable from leaf blade.

FLOWER

Natural flowering season: Spring until Autumn.
Begins flowering after how many years/months: 2 months.
Inflorescence type and habit: Raceme.
Rate of flower opening: Approximately 1 day from bud to fully opened flower.
Flower longevity on plant: 4 days, after fully opened.
Quantity of flowers: 3-5.
Inflorescence size:
- *Diameter*.—Approximately 15 cm.
- *Length*.—Approximately 15 cm.

Peduncle:
- *Length*.—3 cm.
- *Diameter*.—0.2 cm.

Petals:
- *Petal arrangement*.—Rotate, overlapping.
- *Size*.—Medium.
- *Length*.—2 cm.
- *Width*.—2 cm.
- *Shape*.—Broad ovate.
- *Margin*.—Weak reflexing of margin, entire to mildly lobed.
- *Apex*.—Shallowly lobed.
- *Base*.—Obtuse.
- *Petal quantity*.—8.
- *Texture*.—Soft, non pubescent.

Color:
- *Petals*.—When opening: Upper surface: Near Red RHS 56C. blotch near Red-Purple 61B. Lower surface: Near Yellow-Orange RHS 22D. Fully opened: Upper surface: Near Red RHS 56C, blotch near Red-Purple 61B. Lower surface: Near Yellow-Orange RHS 22D. Color Changes when aging: Changing to Near Purple RHS 76D.

Bud:
- *Shape*.—Round.
- *Length*.—Approximately 1.5 cm.
- *Diameter*.—Approximately 1 cm.
- *Color*.—Near Red RHS 756C.

Sepal:
- *Length*.—1 cm.
- *Width*.—0.4 cm.
- *Shape*.—Narrow deltoid.
- *Color*.—Interior Surface: Near RHS Green 137A. Exterior Surface: Near RHS Green 137A.
- *Texture*.—Non pubescent. Matte.

Fragrance: None.

REPRODUCTIVE ORGANS

Stamens:
- *Filament length*.—Approximately 0.6 cm.
- *Filament color*.—Near RHS Yellow 10A.

Anthers:

*Length*.—0.2 cm.

*Shape*.—Linear.

*Color*.—Near Yellow-Orange RHS 16D.

*Pollen*.—Color: Near RHS Yellow 9A. Quantity: Many.

Pistil:

*Style*.—Length: Approximately 0.2 cm. Color: Near Green-White RHS 157C.

*Stigma*.—Shape: Linear. Color: Near Green-White RHS 157C.

OTHER CHARACTERISTICS

Seeds and fruits: Not observed to date.

Disease/pest resistance: Good overall disease resistance to normal pests and diseases typical of garden roses.

What is claimed is:

1. A new and distinct cultivar of *Rosa* plant named 'IntRos02' as herein illustrated and described.

* * * * *